United States Patent

Brownfield

[11] 3,938,616
[45] Feb. 17, 1976

[54] SOUND MULTIPLIER

[76] Inventor: Swayze W. Brownfield, c/o George Spector, 3615 Woolworth Bldg., 233 Broadway, New York, N.Y. 10007

[22] Filed: Nov. 27, 1973

[21] Appl. No.: 419,267

[52] U.S. Cl. ............................................. 181/136
[51] Int. Cl.² ........................................ G10K 11/10
[58] Field of Search ......... 181/25, 20, 23, 136, 133, 181/126, 129

[56] References Cited
UNITED STATES PATENTS

| | | |
|---|---|---|
| 698,713 | 4/1902 | Klaws ............................... 181/23 |
| 1,761,666 | 6/1930 | Hinternesch ........................ 181/25 |
| 2,498,239 | 2/1950 | Berkeley ............................. 181/23 |
| 2,537,201 | 1/1951 | Amfitheatrof ...................... 181/25 |
| 3,128,352 | 4/1964 | Cagen ................................ 181/20 |
| 3,637,040 | 1/1972 | Gorman ............................ 181/129 |

Primary Examiner—Stephen J. Tomsky

[57] ABSTRACT

An acoustic amplifier securable detachably to the ears and supported by a head piece to amplify sound without the use of electricity.

1 Claim, 3 Drawing Figures

SOUND MULTIPLIER

SUMMARY OF THE INVENTION

In my invention first and second hollow cuplike members having separate openings are detachably secured to correspondng ears and are interconnected by a curved member resting on the top of the head and extending between the members. Each member has a curved sound reflecting surface which receives sound through an opening aligned in substantially the same plane, as the face of the user and exposing a front edge of an ear.

My invention provides enhanced hearing as compared to that obtainable in the absence of my invention. It can be used as a toy or novelty or for other purposes.

DETAILED DESCRIPTION OF PREFERRED EMBODIMENTS

Figure 1:
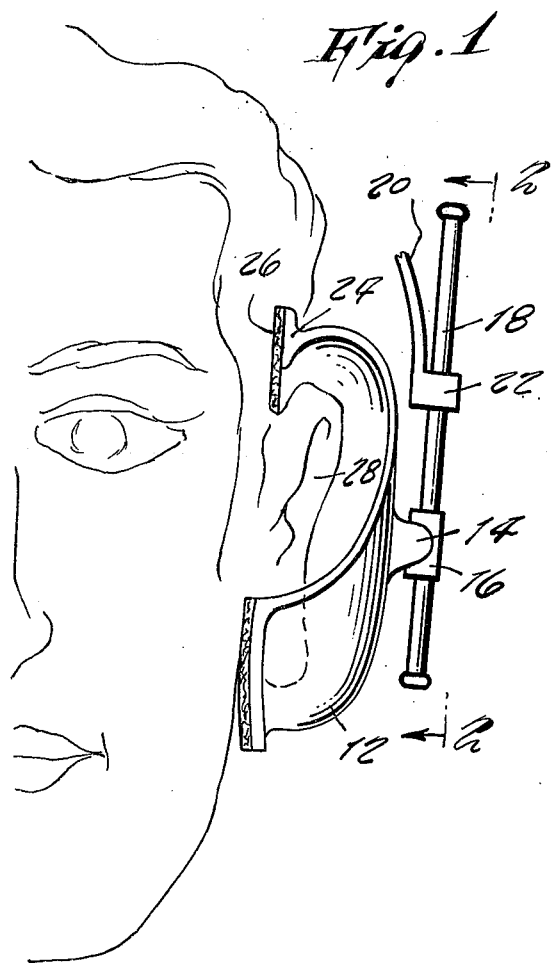
FIG. 1 is a side view showing a portion of my invention in use.
Figure 2:
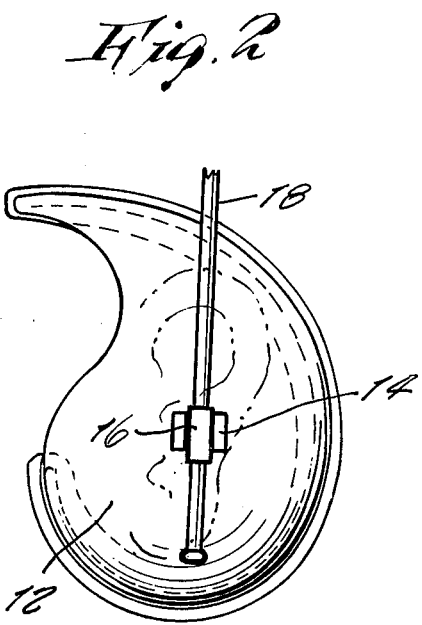
FIG. 2 is a view taken along line 2—2 in FIG. 1.
Figure 3:
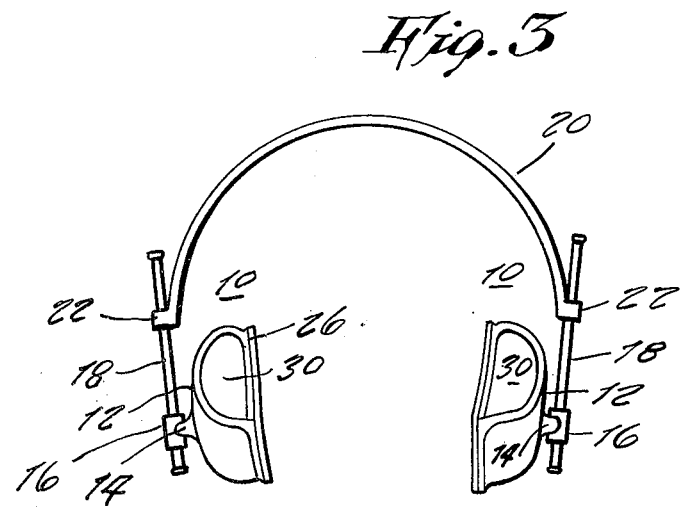
FIG. 3 is a front view of my invention.

Referring now to FIGS. 1-3 left hand right hand cup like members 10 each have an outer surface 12 supporting a post 14 carrying a vertical sleeve 16. A vertical bar 18 is slidable in each sleeve. A curved elongated member 20 has at each enlarged end 22 and enlarged vertical bore in which the corresponding bar 18 is also slidable.

Each member 10 has an outer surface which as viewed in a vertical plane has a spiral contour. Each member has an open section surrounded peripherally by a flange 24 of spiral contour carrying a surface padded with felt 26 which surrounds the ear 28 and contacts the side of the head. Moreover, each member, when in position, has a side opening 30 approximately coincident with the front face of the user. Sound entering opening 30 strikes the oval curved inner sound reflecting surface of cup-like member 12 with the results indicated previously.

While I have described my invention with particular reference to the preferred embodiments and to the drawings, my protection is to be limited only by the terms of the claims which follow:

I claim:

1. A sound amplifier comprising a pair of similar cups adapted to fit over a persons ears, in combination with a fitting adapted to be mounted on a persons head wherein each cup comprises a flat flange of spiral contour adapted to fit sealingly about a persons ear, wherein said flange has an upper end and a spaced lower end connected with an intermediate portion of spiral contour, including an integral outer shell of spiral contour extending outwardly from the flange having a transverse oval curvature providing an enclosure for the ear, said shell having an outer periphery terminating at the ends of the flange and a side opening between the said ends bounded by curved edges, wherein said fitting includes a curved member adjustably mounted on spaced vertical bars, including vertical sleeves projecting from the shells mounted movably on said bars.

* * * * *